US009687189B2

(12) United States Patent
Tafazzoli et al.

(10) Patent No.: US 9,687,189 B2
(45) Date of Patent: Jun. 27, 2017

(54) AUTOMATIC VISUAL REMOTE ASSESSMENT OF MOVEMENT SYMPTOMS IN PEOPLE WITH PARKINSON'S DISEASE FOR MDS-UPDRS FINGER TAPPING TASK

(71) Applicant: Xerox Corporation, Norwalk, CT (US)

(72) Inventors: Faezeh Tafazzoli, Louisville, KY (US); Beilei Xu, Penfield, NY (US); Hao Wu, Pittsford, NY (US); Robert P Loce, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 236 days.

(21) Appl. No.: 14/707,153

(22) Filed: May 8, 2015

(65) Prior Publication Data

US 2016/0089073 A1 Mar. 31, 2016

Related U.S. Application Data

(60) Provisional application No. 62/056,948, filed on Sep. 29, 2014.

(51) Int. Cl.
*A61B 5/00* (2006.01)
*A61B 5/11* (2006.01)
*G06K 9/00* (2006.01)
*G06K 9/32* (2006.01)

(52) U.S. Cl.
CPC .......... *A61B 5/4082* (2013.01); *A61B 5/1128* (2013.01); *A61B 5/7264* (2013.01); *G06K 9/00355* (2013.01); *G06K 9/00744* (2013.01); *G06K 9/3233* (2013.01)

(58) Field of Classification Search
CPC ............... A61B 5/4082; A61B 5/4076; A61B 5/1124–5/1128; A61B 5/7264; G06K 9/00355; G06K 9/00744; G06K 9/3233
See application file for complete search history.

(56) References Cited

PUBLICATIONS

Holmes, Gordon, "The Symptoms of Acute Cerebellar Injuries Due to Gunshot Injuries", 77 pages, Dec. 1917.
Khan, Taha, "A Computer Vision Framework for Finger-Tapping Evaluation in Parkinson's Disease", 14 pages, Artificial Intelligence in Medicine xxx (2013) xxx-xxx, Nov. 4, 2013.
Hsieh,Chen-Chiung, "Enhanced Face-Based Adaptive Skin Color Model", pp. 167-176, 2012, Journal of Applied Science and Engineering, vol. 15, No. 2.
Gandhi, Rajiv, "Fusion of Skin Color Detection and Background Subtraction for Hand Gesture Segmentation", vol. 3, Issue 2, Feb. 2014, International Journal of Engineering Research & Technology, pp. 1835-1839.

*Primary Examiner* — Scott Getzow
(74) *Attorney, Agent, or Firm* — Fay Sharpe LLP (57) ABSTRACT

A system and method for assessing patient movement for Parkinson's disease includes capturing a video of a subject performing a finger tapping sequence comprising a predetermined number of open and close periods. According to an exemplary embodiment, a system and method includes extracting a region of interest for each frame of the video and generating a projection of the region of interest for each frame of the video using perpendicular vector projections in a direction or plurality of directions.

20 Claims, 9 Drawing Sheets
(7 of 9 Drawing Sheet(s) Filed in Color)

AUTOMATIC VISUAL REMOTE ASSESSMENT OF MOVEMENT SYMPTOMS IN PEOPLE WITH PARKINSON'S DISEASE FOR MDS-UPDRS FINGER TAPPING TASK

This application claims priority to U.S. Provisional Patent Application No. 62/056,948, filed Sep. 29, 2014, by Faezeh Tafazzoli et al., entitled "AUTOMATIC VISUAL REMOTE ASSESSMENT OF MOVEMENT SYMPTOMS IN PEOPLE WITH PARKINSON'S DISEASE FOR MDS-UPDRS FINGER TAPPING TASK" and is incorporated herein by reference in its entirety.

BACKGROUND

This disclosure relates to methods and system to detect hand motions. According to one specific exemplary embodiment, provided is a system and method relating to the diagnosis of Parkinson's disease with a diagnosis metric.

Parkinson's disease (PD) is a progressive and incurable disease and results in considerable utilization of health and community services. Currently, about 1 million Americans or about 1 percent of the population over 60 years of age, are suffering from this disease and this number is expected to rise fourfold by 2040. The cost per patient per year in USA is around 10,000 USD. PD, the second most universal chronic neurodegenerative disease after Alzheimer's disease, is characterized by the loss of dopaminergic neurons in brain. The loss results in dysfunction of circuitries that are responsible for motor and cognitive functions. The key motor symptom is restriction of mobility that reveals as bradykinesia, rigidity, rest tremor, and postural instability. Bradykinesia, i.e., slowness and decrement in movement, is the major symptom of PD and is, therefore, crucial for diagnosis and for estimating the severity of the patient's functional disability.

Reliable clinical evaluations are important, as patients need to be followed up with frequent treatment adjustments for many years. Medicine dosing may need to be adjusted with respect to patient's performance in order to slow down the loss of dopamine.

The motor clinical characteristics of PD are usually quantified by physicians using validated clinical scales such as Unified Parkinson's Disease Rating (UPDRS). The examination requires the Specialists in Movement Disorders (SMDs) to score motor disturbances on a 5-point scale ranging from 0 (normal performance) to 4 (severe, unable to perform the task) on the basis of visual inspection. However, the assessment is subjective and requires considerable experience and monitoring to minimize variability among different raters. Analyzing finger tapping movement is a prevalent evaluation method used in clinics for motor function estimation due to the fact that the rhythm of the movements acts as an efficient index for cerebellar function testing. See G. Holmes, "The symptoms of acute cerebellar injuries due to gunshot injuries", Brain, vol. 40, No. 4, pp. 461-535, 1917.

The periodic rhythm of the dominant hand finger movements acts as an efficient index for evaluation of brain motor function. To achieve a reliable, quantitative and objective clinical assessment, previously published scientific works use electrocardiographic apparatuses, accelerometers, gyroscopes, lightweight magnetic sensors, camera systems with active/passive markers and 3D images captured from infrared cameras. Some of this equipment can influence the results due to their weight, unnatural form, and the connected wires, which can be invasive and distracting. Also, the equipment is expensive and/or requires supervision.

Another approach to assessment is via telemedicine and remote viewing by a specialist. This remote delivery of healthcare services and clinical information using telecommunications technology is especially valuable to chronically ill patients in remote, rural and underserved areas who may not otherwise receive such care. In case of PD, 42% of the patients don't get the specialized care of a neurologist, which places these individuals at a great risk. Thus, PD particularly lends itself to telemedicine because, as mentioned earlier, many aspects of the diagnosis and treatment process are on the basis of visual inspection. While televiewing provides advances, it does not address the issue of the relative lack of qualified healthcare practitioners to the population for current protocols, and doesn't address the desire for increased numbers of assessments of the desired protocols, i.e., regular monitoring under a variety of conditions and to test new protocols. Further, it also does not eliminate the rater variability issue.

A cost-efficient system and methodology for objective measurement of these variables for a patient performing the task in front of a camera at home or at a clinic is desired.

INCORPORATION BY REFERENCE

G. Holmes, "The symptoms of acute cerebellar injuries due to gunshot injuries", Brain, vol. 40, No. 4, pages 461-535, 1917;

T. Khan, D. Nyholm, J. Westin and M. Dougherty, "A computer vision framework for finger-tapping evaluation in Parkinson's disease". Artificial Intelligence in Medicine, Vol. 60, No. 1, pages 27-40, 2014;

S. N. Karishma and V. Lathasree, "Fusion of Skin Color Detection and Background Subtraction for Hand Gesture Segmentation", International Journal of Engineering Research & Technology, Vol. 3, No. 2, 2014; and C. Hsieh, D. Liou and w. Lai, "Enhanced Face-Based Adaptive Skin Color Model", Journal of Applied Science and Engineering, Vol. 15, No. 2, pages 167-176, 2012, are incorporated herein by reference in their entirety.

BRIEF DESCRIPTION

In one embodiment of this disclosure, described is a method for assessing patient movement, comprising: capturing a video of a subject performing a finger tapping sequence comprising a predetermined number of open and close periods; extracting a region of interest for each frame of the video; generating one or more projections of the region of interest for each frame of the video using perpendicular vector projections in a direction; extracting maximums and minimums over time from the generated projections; extracting temporal features from the extracted maximums and minimums; and mapping the extracted temporal features to a trained model to attach an assessment to the subject.

In another embodiment of this disclosure, described is a motion assessment system, comprising: one or more image capturing devices configured to capture a video of a finger tapping sequence comprising a predetermined number of open and close periods; a ROI (Region of Interest) module for tracking extracting a region of interest for each frame of the video; a memory having instructions to be performed by one or more processors, the instructions including the steps of: extracting a region of interest for each frame of the video; generating one or more projections of the region of interest for each frame of the video using perpendicular vector projections in a direction; and extracting maximums and minimums over time from the generated projections.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

An exemplary method and system according to this disclosure is now described with reference to FIG. 1 and FIG. 2, respectively based on UPDRS instructions for finger tapping where a patient is instructed to tap their index finger on their thumb 10 times as quickly and as big as they possibly can.

Figure 1:
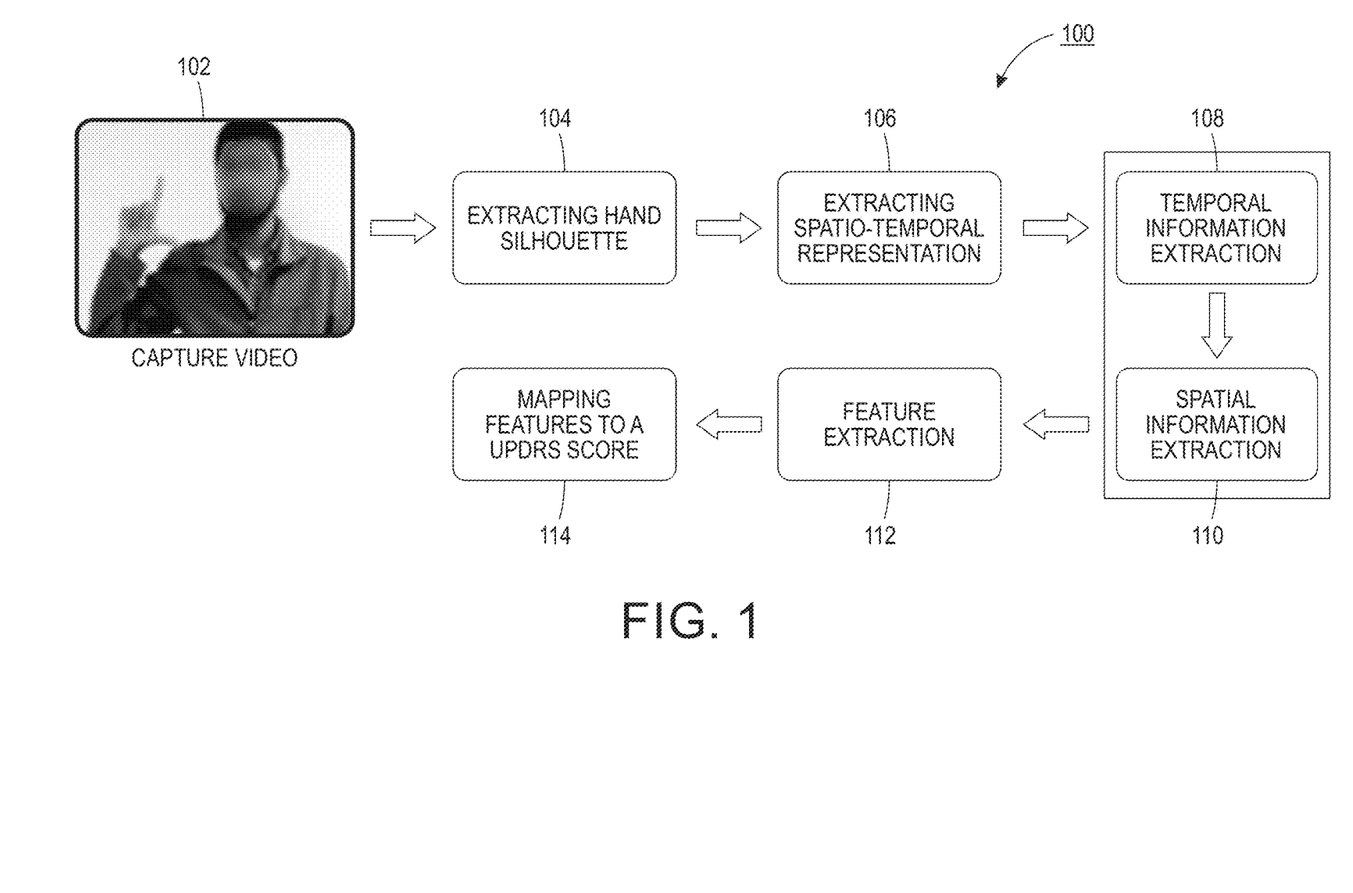
FIG. 1 is an exemplary flowchart for assessing patient movement.

With reference to FIG. 1, a flowchart of the exemplary method 100 is shown. The listed steps below are described in further detail below. The method includes:

a) capturing video 102 including a clear view of a patient's hand movement using a video imaging system;

b) extracting a hand silhouette 104, i.e., a region of interest around the hand, and tracking the hand during the sequence;

c) creating spatio-temporal representations 106 of the task for different projections of silhouette extracted from various directions;

d) extracting temporal information 108 for determining the times when the index and thumb fingers have the maximum and minimum distance;

e) extracting spatial information 110 for determining the location of index and thumb fingers at frames in which fingers have the maximum and minimum distance by infusing information of the spatio-temporal data of the projection which displays the maximum change in index finger's location and the one displaying major changes in both fingers;

f) extracting features 112 such as number of interruptions, pace of slowing and index of amplitude decrement from the information extracted in the previous two steps; and g) mapping features 114 to an equivalent 0-4 UPDRS score.

Figure 2:
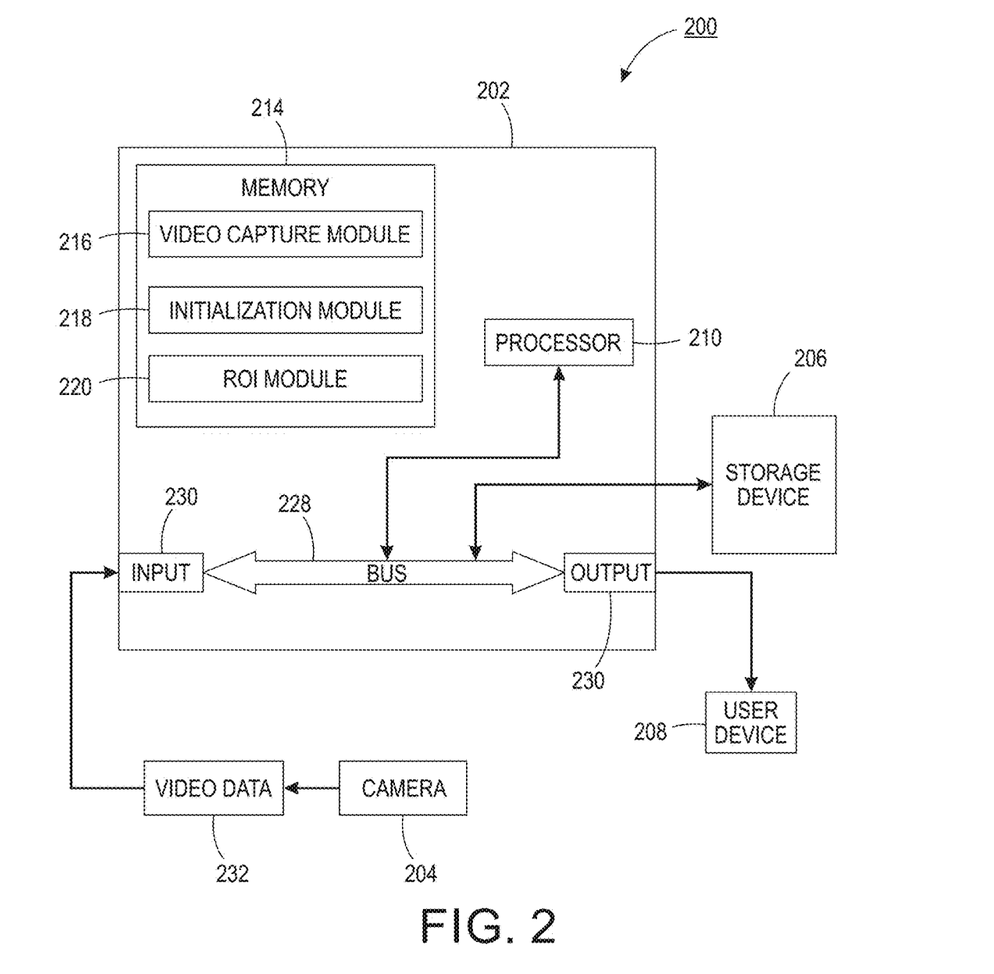
FIG. 2 is a video processing system for assessing patient movement, according to an exemplary embodiment of this disclosure.

With reference to FIG. 2, illustrated is a schematical representation of an exemplary video capturing and processing system 200 including an exemplary algorithm to assess movement symptoms according to an exemplary embodiment of this disclosure.

The video capturing and processing system 200 includes a video processing device 202, a video capture device 204, and a storage device 206, which may be linked together by communication links, referred to herein as a network. In one exemplary embodiment, the system 200 may be in further communication with a user device 208. These components are described in greater detail below.

Video processing device 202 illustrated in FIG. 2 includes a controller that is part of or associated with the video processing device 202. The exemplary controller is adapted for controlling an analysis of video data received by the system 200. The controller includes a processor 210, which controls the overall operation of the image processing device 202 by execution of processing instructions that are stored in memory 214 connected to the processor 210.

Memory 214 may represent any type of tangible computer readable medium such as random access memory (RAM), read only memory (ROM), magnetic disk or tape, optical disk, flash memory, or holographic memory. In one embodiment, the memory 214 includes a combination of random access memory and read only memory. The digital processor 210 can be variously embodied, such as by a single-core processor, a dual-core processor (or more generally by a multiple-core processor), a digital processor and cooperating math coprocessor, a digital controller, or the like. The digital processor, in addition to controlling the operation of the video processing device 202, executes instructions stored in memory 214 for performing the parts of a method discussed herein. In some embodiments, the processor 210 and memory 214 may be combined in a single chip.

The video processing device 202 may be embodied in a networked device, such as the video capture device 204, although it is also contemplated that the video processing device 202 may be located elsewhere on a network to which the system 200 is connected, such as on a central server, a networked computer, or the like, or distributed throughout the network or otherwise accessible thereto. The functions of the video processing device 202 can be performed remotely away from the subject of the video. The video data analysis, i.e., movement symptom analysis include spatial-temporal analysis, phases disclosed herein are performed by the processor 210 according to the instructions contained in the memory 214. In particular, the memory 214 stores a video capture module 216, which captures video data of a finger tapping test; an initialization module 218, which initializes the system; and a ROI module 220, which detects and tracks objects that are moving in the area of interest. Embodiments are contemplated wherein these instructions can be stored in a single module or as multiple modules embodied in the different devices.

The software modules as used herein, are intended to encompass any collection or set of instructions executable by the video processing device 202 or other digital system so as to configure the computer or other digital system to perform the task that is the intent of the software. The term "software" as used herein is intended to encompass such instructions stored in storage medium such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server (not shown) or other location to perform certain functions. The various components of the video processing device 202 may be all connected by a bus 228.

With continued reference to FIG. 2, the video processing device 202 also includes one or more communication interfaces 230, such as network interfaces, for communicating with external devices. The communication interfaces 230 may include, for example, a modem, a router, a cable, and/or Ethernet port, etc. The communication interfaces 230 are adapted to receive video and/or image data 232 as input.

The video processing device 202 may include one or more special purpose or general purpose computing devices, such as a server computer or digital front end (DFE), or any other computing device capable of executing instructions for performing the exemplary method.

FIG. 2 further illustrates the video processing device 202 connected to a video source 204 for inputting and/or receiving the video data and/or image data (hereinafter collectively referred to as "video data") in electronic format. The video source 204 may include an image capture device, such as a camera. The video source 204 can include one or more cameras that capture video data of the area of interest.

In one embodiment, the video source 204 can be a device adapted to relay and/or transmit the video captured by the camera to the video processing device 202. For example, the video source 204 can include a scanner, a computer, or the like. In another embodiment, the video data 232 may be input from any suitable source, such as a workstation, a database, a memory storage device, such as a disk, or the like. The video source 204 is in communication with the controller containing the processor 210 and memories 214.

With continued reference to FIG. 2, the system 200 includes a storage device 206 that is part of or in communication with the video processing device 202. In a contemplated embodiment, the video processing device 202 can be in communication with a server (not shown) that includes a processing device and memory, such as storage device 206.

Various aspects of the method and system of detecting movement symptoms are now described in further detail.

With continuing reference to FIG. 1, video of a subject, i.e., a patient or person to be assessed, is captured 102 while the subject performs a finger tapping test using the video source 204. The video data 232 is input into the video processing system 202 and stored in the video capture module 216 of the memory 214 of the video processing system 202. According to an exemplary embodiment, the finger tapping test includes ten fast repetitions of the subject bringing the index finger to the thumb and then bringing the two fingers as wide as the subject can. It is to be understood that while the exemplary embodiment described herein includes ten finger taps, more or less finger taps may be used, for example, but not limited to, 3-7 finger taps and/or 11-20 finger taps. Common video acquisition devices can be used, such as web cams, smart phones, or specialized video cameras. The video data is handled in one or more of several ways. For instance, it can be stored locally, e.g., disk, flash drive, and the like, for subsequent processing, sent to a server for processing, processed locally, and the results sent to a healthcare provider. In one embodiment, transmission and storage accounts for HIPAA requirements.

In each video frame, the processor 210 extracts a region of interest, i.e., including a hand 104. In one embodiment, the region of interest is extracted by detecting the face of the patient, i.e., subject, and using the size, location, and color of the face bounding box. The size of the ROI is determined proportional to the size of the face of the subject because the length of an adult person's hand is approximately equal to the height of that person's face. See T. Khan, D. Nyholm, J. Westin and M. Dougherty, "A computer vision framework for finger-tapping evaluation in Parkinson's disease". Artificial Intelligence in Medicine, Vol. 60, No. 1, pp. 27-40, 2014. In another embodiment, the size of the ROI is determined by detecting skin of the subject directly from each frame.

The processor 210 uses skin color and motion data, detected from the hand in each ROI and tracked throughout the entire sequence. See S. N. Karishma and V. Lathasree, "Fusion of Skin Color Detection and Background Subtraction for Hand Gesture Segmentation", International Journal of Engineering Research & Technology, Vol. 3, No. 2, 2014.

For detecting the skin, a face-based adaptive threshold using a personalized Gaussian skin color model can be employed to account for illumination variations. See C. Hsieh, D. Liou and w. Lai, "Enhanced Face-Based Adaptive Skin Color Model", Journal of Applied Science and Engineering, Vol. 15, No. 2, pp. 167-176, 2012.

Figure 3:
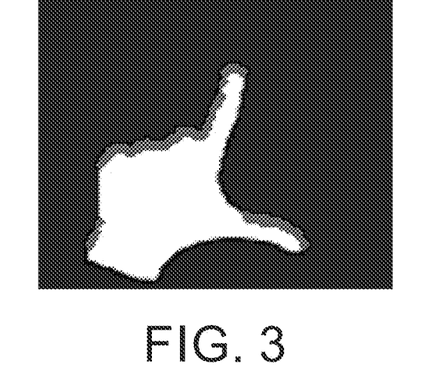
FIGS. 3-8 depict perpendicular vector projections and corresponding spatial plots of a single frame in a video sequence, according to an exemplary embodiment of this disclosure.
Figure 4:
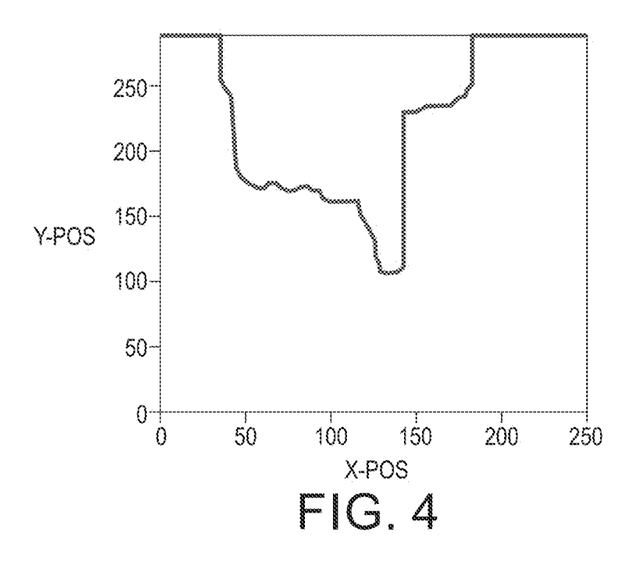
Figure 5:
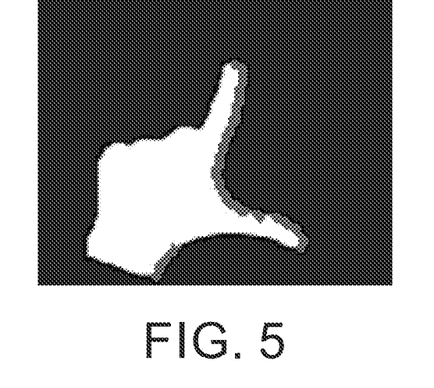
Figure 6:
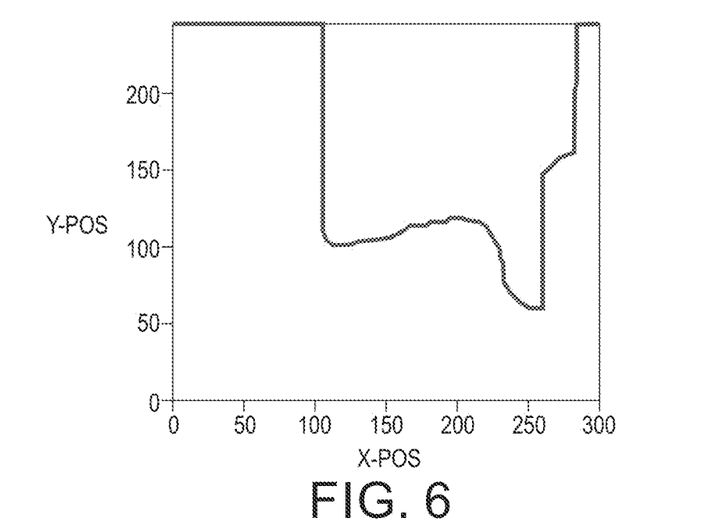
Figure 7:
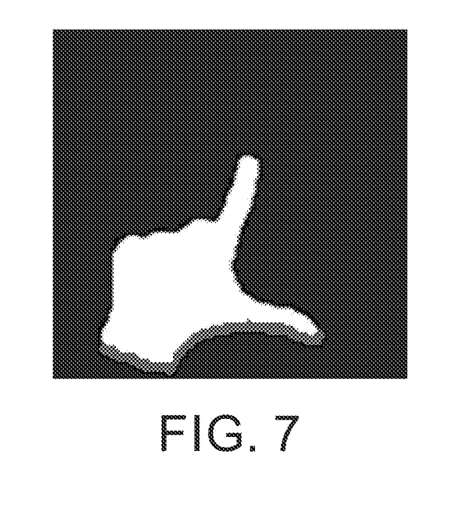
Figure 8:
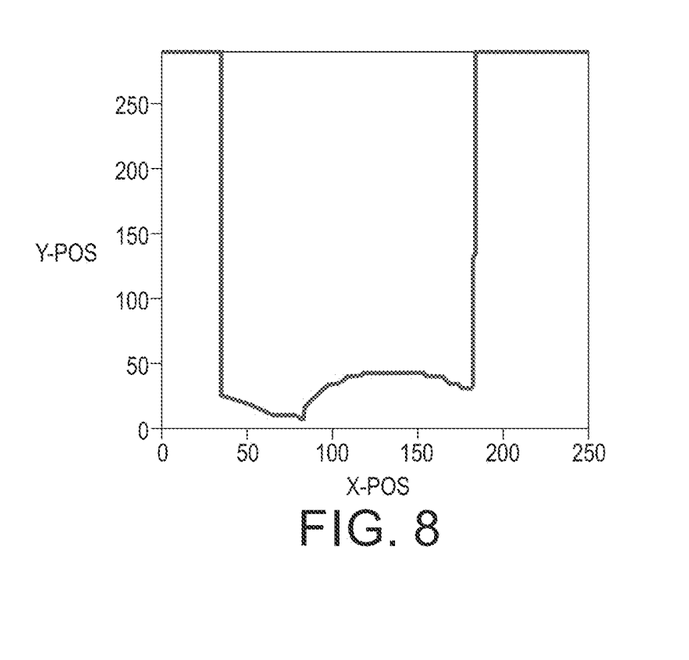

The processor 210 extracts spatio-temporal representations 106 for the entire video sequence from the silhouette of the hand detected in each frame of the video. With reference to FIGS. 3, 4, 5, 6, 7, and 8, the representation is based on different projections of each silhouette in different directions. For each frame of the video, the projection of a specific direction, i.e., top, right, or bottom, is the perpendicular distance of each point from the silhouette to the border of the ROI. The projections are shown as red areas in FIGS. 3, 5, and 7. FIG. 3 depicts a silhouette of a ROI for one frame with a perpendicular vector projection, i.e., red pixels/dots, for the top of the silhouette. The top projection represents the red pixels/dots of FIG. 3 in a position graph depicted in FIG. 4, with the x-axis representing the horizontal position of the top projection and the y-axis representing the inverse vertical position of the top projection. FIG. 5 depicts a right projection of the same frame with FIG. 6 representing the corresponding position graph of the red pixels/dots. FIG. 7 depicts a bottom projection of the same fame with FIG. 8 representing the corresponding position graph of the red pixels/dots.

Figure 9:
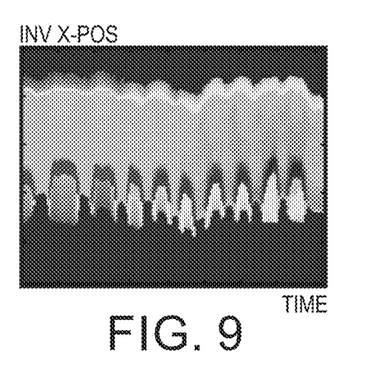
FIGS. 9-11 depict spatio-temporal projections of an entire video sequence for different projected directions, according to an exemplary embodiment of this disclosure.
Figure 10:
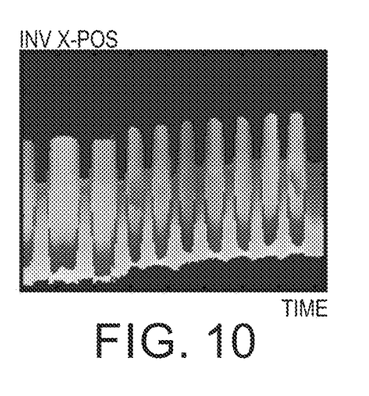
Figure 11:
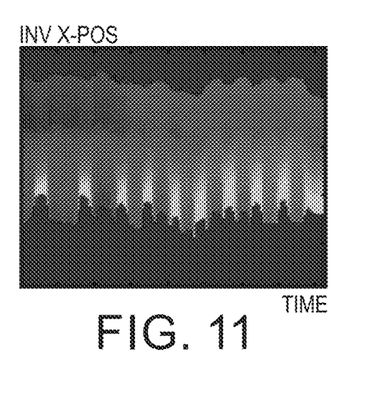

With reference to FIGS. 9, 10, and 11, for each projection, the processor 210 accumulates the projection vectors through the entire video sequence for all frames and creates a spatio-temporal presentation 106 for each direction, i.e., top, right, and bottom for this exemplary embodiment. To create the spatio-temporal presentation, the processor 210 assigns a value corresponding to the y-axis position value of the projection along the x-axis position value. In one embodiment, the assigned value is a color, e.g. red hues for high y-axis values and blue hues for lower y-axis values. In another embodiment, the assigned values correspond to gray-scale pixel intensities. FIG. 9 shows accumulated top projections from each frame of the video sequence where one column of the graph represents one projection of one frame and the bottom axis represents the time in the video sequence. FIGS. 10 and 11 depict spatio-temporal representations of the right and bottom projections respectively. In one embodiment, the processor 210 accounts for the subject keeping the hand in different orientations each time by finding the representation, i.e., projection direction, that displays a tapping pattern with maximum changes between open and closed status of fingers. In another embodiment, an average of the spatio-temporal representations in each direction is used. In another embodiment, the optimal direction angle that creates the best periodic pattern, i.e., fluctuations between open and closed orientations, is determined and used.

Figure 12:
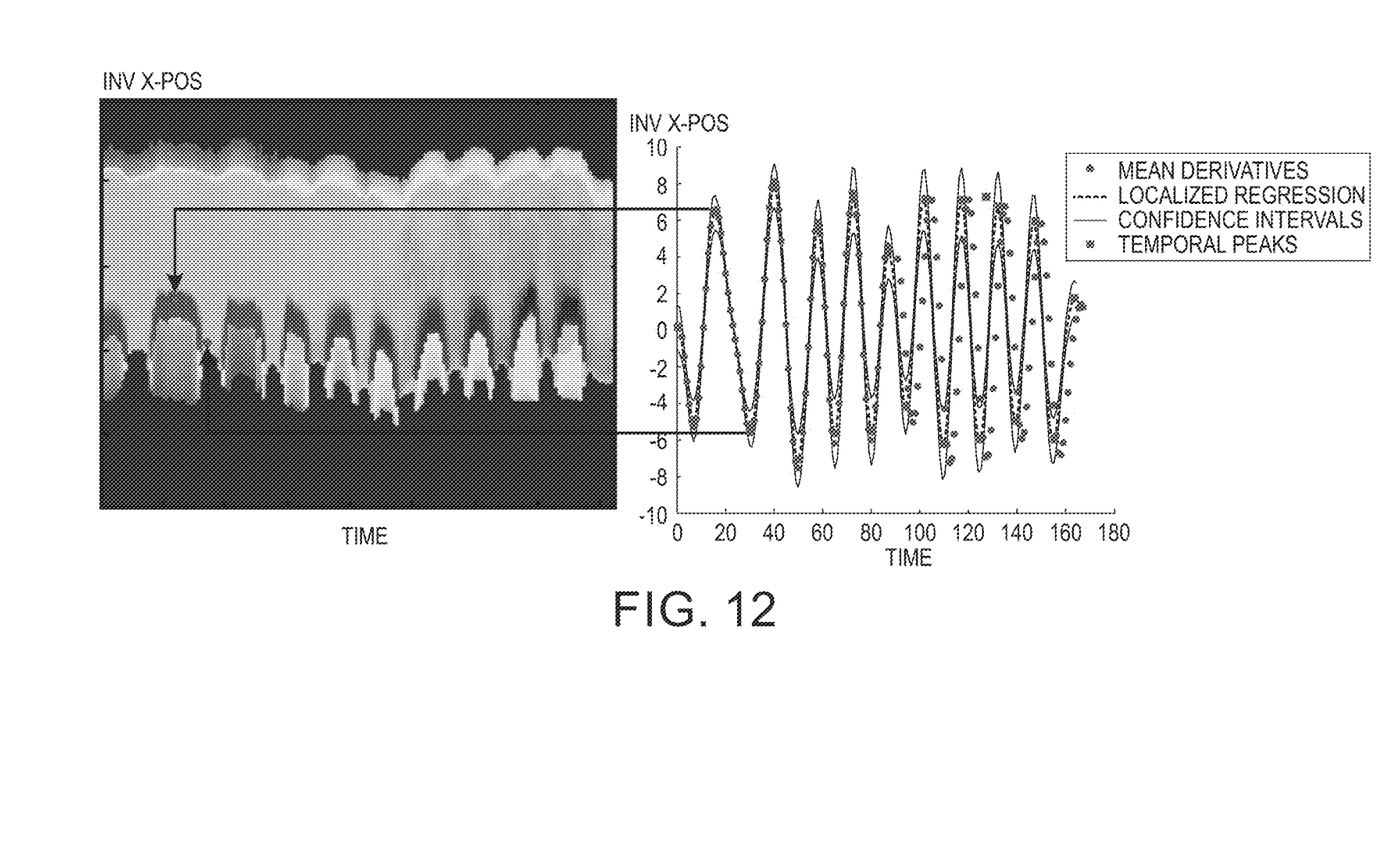
FIG. 12 depicts a generated time stamp graph, according to an exemplary embodiment of this disclosure.

The processor 210 determines the location of fingers at their extreme positions, i.e., either opened or closed, in time. The processor 210 extracts temporal information of the points where the fingers are in the full open or closed position. The processor 210 finds the spatio-temporal data that displays the maximum vertical change in the index finger. From this spatio-temporal pattern, i.e., FIGS. 9, 10, and 11, the processor extracts the points in time 108 where maximum changes have occurred. With reference to FIG. 12, the processor 210 pre-processes the spatio-temporal pattern to remove noise and fluctuations repeated due to hand shaking. The processor 210 generates a time stamp graph 1202 by applying a non-parametric regression on averaged derivatives. The local minimums and maximums of the time stamp graph 1202 represent the time stamp of the start and end of each finger-tapping cycle.

From the temporal information indicating start and end of each finger tapping cycle, the processor 210 extracts the location of the fingertips 110, where the pattern displays a wide open or completely closed state for fingers depending on a peak or valley in the time stamp graph 1202. The processor 210 combines the temporal information with other spatio-temporal data that represents a horizontal projection of silhouette displaying maximum change in location of both thumb and index finger.

Figure 13:
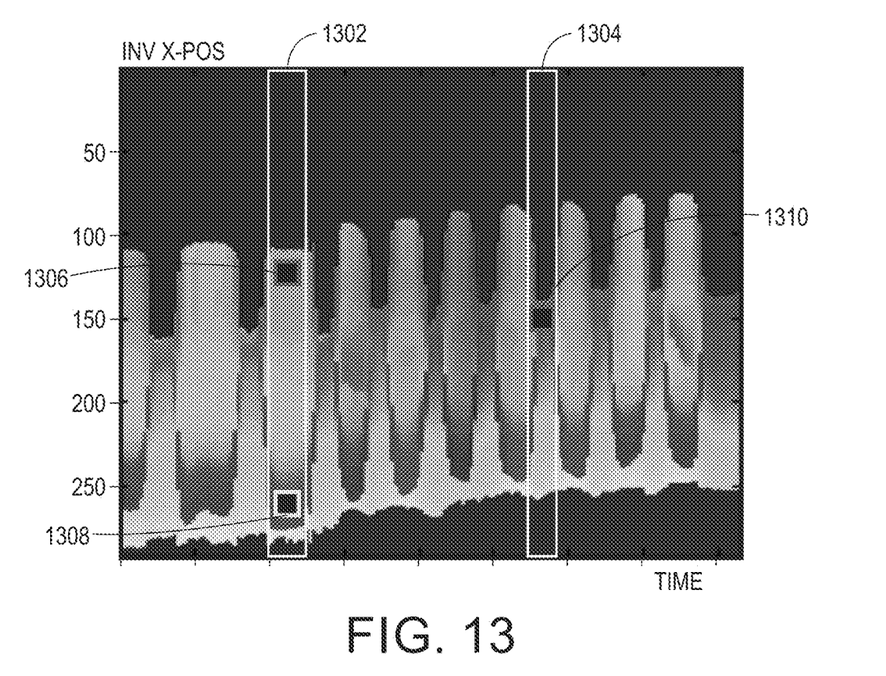
FIG. 13 depicts a segmented spatio-temporal projection, according to an exemplary embodiment of this disclosure.

The processor 210 selects a window 1302, 1304 around each point that has the height of the spatio-temporal pattern and a varying width depending on the distance between two consecutive peaks. With reference to FIG. 13, the selected image in each window 1302, 1304 is segmented into three or two regions depending on having a peak window 1302 or valley window 1304 respectively. A peak window 1302 corresponds to the index finger and thumb apart, and therefore two cluster boxes are selected indicating the location of index finger 1306 and the thumb 1308 respectively. A valley window 1304 corresponds to the index finger and thumb together, and therefore one cluster box 1310 is selected. The processor 210 determines the position of index finger and thumb using an average location in the related cluster boxes and based on the fact that the thumb is always located below the index finger. The processor 210 repeats the window selection for each local minimum and maximum time stamp to determine the location of the thumb and index fingers at the extreme points, i.e., opened and closed, during the video sequence, i.e., the finger tapping task.

The processor 210 extracts features from the finger tapping task 112 based on a discrete scale of the UPDRS evaluation which can be assigned to the patient's current status. The extracted features can include number of interruptions, pace of slowing the task, the time at which the amplitude starts to decrement and the like.

Figure 14:
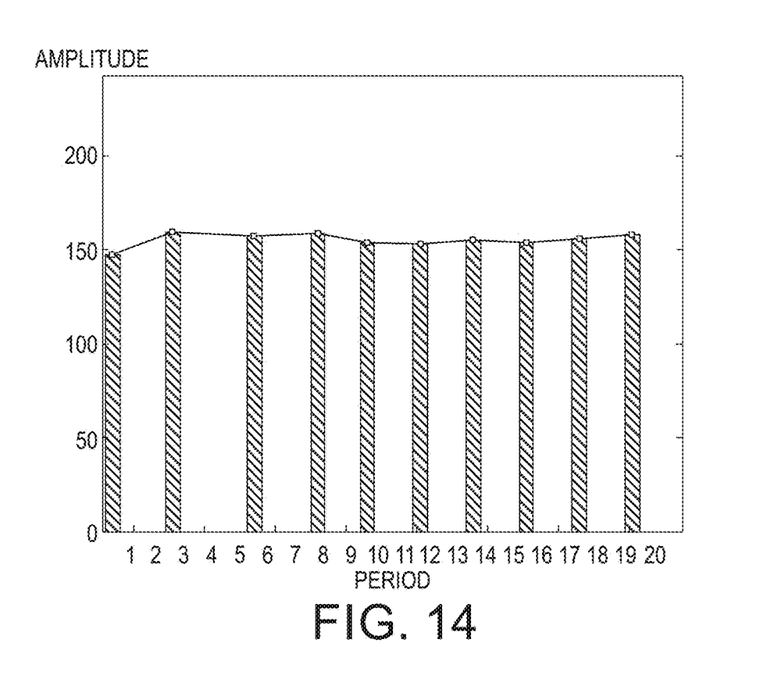
FIG. 14 depicts an amplitude plot of time intervals, according to an exemplary embodiment of this disclosure.
Figure 15:
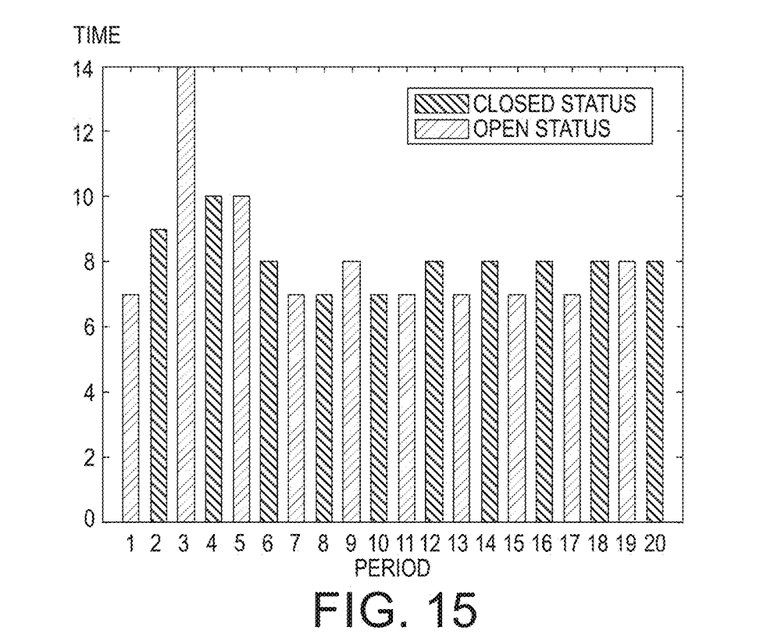
FIG. 15 depicts a time vs. period chart of extreme positions, according to an exemplary embodiment of this disclosure.

The processor 210 determines the location of index finger and thumb at specific time intervals during the whole sequence and analyzes the variation of distance between them. The temporal information of extreme points is used by the processor 210 to determine the amount of time the subject has kept his fingers in the closed or open status. This provides a presentation of the period of each status resulting in an inference for the number of interruptions occurred. In one embodiment, with reference to FIG. 14, the processor 210 creates an amplitude plot of the time intervals to determine a decrement time, if any, which is a UPDRS factor. In another embodiment, with reference to FIG. 15, the processor 210 creates a time vs. period chart indicating the amount of time spent in each determined extreme, open and closed, position.

The processor 210 inputs the extracted feature data into a trained model to classify each graph to a discrete number/value for each patient 114. The values for each feature have are presented in the table below.

| 0: Normal | 1: Slight | 2: Mild | 3: Moderate | 4: Severe |
| --- | --- | --- | --- | --- |
| No problems | a) 1 or 2 interruptions or hesitations<br>b) Slight slowing<br>c) Amplitude decrements near the end of the 10 taps | a) 3 to 5 interruptions<br>b) Mild slowing<br>c) Amplitude decrements midway in the task | a) More than 5 interruptions or at least one longer arrest (freeze) in ongoing movement<br>b) Moderate slowing<br>c) Amplitude decrements starting after the 1st tap | a) Cannot or can only barely perform the task because of slowing, interruptions or decrements |

The number indicating the stage of the disease should be assigned if any of the conditions are met. The numbers of the table indicate the patient's UPDRS score for determination of Parkinson's disease.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A computer implemented method for assessing patient movement, comprising:
    capturing a video including a plurality of frames of a subject performing a finger tapping sequence including a predetermined number of open and close periods;
    extracting a region of interest for each frame of the video;
    generating one or more projections of the region of interest for a set of frames; and
    extracting maximums and minimums over time from the generated projections.

2. The computer implemented method according to claim 1, further comprising:
    extracting temporal features from the extracted maximums and minimums; and
    mapping the extracted temporal features to a trained model to attach an assessment to the subject.

3. The computer implemented method according to claim 2, wherein the extracted temporal features is one of number of interruptions, pace of slowing the task, the time at which the amplitude starts to decrement.

4. The computer implemented method according to claim 2, wherein the trained model represents a UPDRS score for diagnosing Parkinson's disease.

5. The computer implemented method according to claim 1, wherein generating a projection of the region of interest includes using perpendicular vector projections for a border of the region of interest facing a direction.

6. The computer implemented method according to claim 1, wherein extracting maximums and minimums includes:
    constructing a spatio-temporal representation of the video based on the projections for the direction;
    extracting temporal data from the spatio-temporal representation to generate a time stamp graph having local minima and maxima indicating a start and end time of each open/close period; and
    extracting spatial data to determine one of an open or closed position depending on the local minima and maxima of the time stamp graph.

7. The computer implemented method according to claim 6, wherein the spatio-temporal representation represents the spatial position of a pixel of the projection along the vertical axis and the time of the frame of the video along the horizontal axis.

8. The computer implemented method according to claim 6, wherein constructing the spatio-temporal representation includes assigning a visual indicator value corresponding to the vertical spatial coordinates of the projection.

9. The computer implemented method according to claim 6, wherein extracting the spatial data includes:
    combining the temporal data with another spatio-temporal representation to determine an open or closed state;
    selecting a window around each local minimum and maximum representing the height of the spatio-temporal representation; and
    determining the position of the thumb and index finger using an average location in the window.

10. A computer program product comprising tangible media with encoded instructions for performing the method of claim 1.

11. A system for assessing movement symptoms in a video comprising:
    a video processing system including memory which stores instructions for performing the method of claim 1 and a processor in communication with the memory for executing the instructions.

12. A motion assessment system, comprising:
    one or more image capturing devices configured to capture a video of a finger tapping sequence comprising a predetermined number of open and close periods;

a ROI module for tracking extracting a region of interest for each frame of the video; and a memory having instructions to be performed by one or more processors, the instructions including the steps of:
    extracting a region of interest for each frame of the video;
    generating one or more projections of the region of interest for a set of frames; and
    extracting maximums and minimums over time from the generated projections.

13. The motion assessment system according to claim 12, the instructions further comprising:
    extracting temporal features from the extracted maximums and minimums; and
    mapping the extracted temporal features to a trained model to attach an assessment to the subject.

14. The motion assessment system according to claim 13, wherein the extracted temporal features is one of number of interruptions, pace of slowing the task, the time at which the amplitude starts to decrement.

15. The motion assessment system according to claim 13, wherein the trained model represents a UPDRS score for diagnosing Parkinson's disease.

16. The motion assessment system according to claim 12, the instructions for generating a projection of the region of interest includes using perpendicular vector projections for a border of the region of interest facing a direction.

17. The motion assessment system according to claim 12, the instructions for extracting maximums and minimums comprises:
    constructing a spatio-temporal representation of the entire video based on the projections for the direction;
    extracting temporal data from the spatio-temporal representation to generate a time stamp graph having local minima and maxima indicating a start and end time of each open/close period; and
    extracting spatial data to determine one of an open or closed position depending on the local minima and maxima of the time stamp graph.

18. The motion assessment system according to claim 17, wherein the spatio-temporal representation represents the spatial position of a pixel of the projection along the vertical axis and the time of the frame of the video along the horizontal axis.

19. The motion assessment system according to claim 17, wherein the instructions for constructing the spatio-temporal representation includes assigning a visual indicator value corresponding to the vertical spatial coordinates of the projection.

20. The motion assessment system according to claim 17, wherein the instructions for extracting the spatial data includes:
    combining the temporal data with another spatio-temporal representation to determine an open or closed state;
    selecting a window around each local minimum and maximum representing the height of the spatio-temporal representation; and
    determining the position of the thumb and index finger using an average location in the window.

* * * * *